United States Patent [19]
Wilkes

[11] Patent Number: 5,976,397
[45] Date of Patent: Nov. 2, 1999

[54] PHOTOFADING INHIBITOR DERIVATIVES AND THEIR USE IN FABRIC TREATMENT COMPOSITIONS

[75] Inventor: Ian Paul Wilkes, Chester, United Kingdom

[73] Assignee: Lever Brothers Company, New York, N.Y.

[21] Appl. No.: 08/938,772

[22] Filed: Sep. 26, 1997

[30] Foreign Application Priority Data

Sep. 26, 1996 [GB] United Kingdom ............. 9620093

[51] Int. Cl.$^6$ .............. C09K 15/04; C11D 3/16
[52] U.S. Cl. ............ 252/8.91; 8/442; 252/8.61; 252/399; 252/400.1; 252/401; 252/402; 252/403; 252/405; 252/406; 252/407; 252/582; 252/588; 510/276; 510/394; 510/504; 510/505; 510/513
[58] Field of Search ............ 252/8.61, 8.91, 252/582, 588, 399, 400.1, 401, 402, 403, 405, 406, 407; 8/442; 510/276, 394, 504, 505, 513, 531

[56] References Cited

U.S. PATENT DOCUMENTS

| | | | |
|---|---|---|---|
| 4,256,817 | 3/1981 | Hara et al. | 430/17 |
| 4,271,252 | 6/1981 | Hara et al. | 430/216 |
| 4,664,839 | 5/1987 | Rieck | 252/175 |
| 4,686,063 | 8/1987 | Burns | 510/375 |
| 4,751,015 | 6/1988 | Humphreys et al. | 510/376 |
| 4,788,054 | 11/1988 | Bernhardt et al. | 424/59 |
| 4,818,426 | 4/1989 | Humphreys et al. | 510/375 |
| 4,820,439 | 4/1989 | Rieck | 510/469 |
| 4,855,281 | 8/1989 | Byers | 503/227 |
| 4,919,811 | 4/1990 | Davis | 210/500.36 |
| 5,061,807 | 10/1991 | Gethoffer et al. | 548/473 |
| 5,397,501 | 3/1995 | Coope | 252/186.42 |
| 5,571,765 | 11/1996 | VanMaele et al. | 503/227 |

FOREIGN PATENT DOCUMENTS

| | | |
|---|---|---|
| 0239910 | 10/1987 | European Pat. Off. . |
| 0284292 | 9/1988 | European Pat. Off. . |
| 0303520 | 2/1989 | European Pat. Off. . |
| 0325288 | 7/1989 | European Pat. Off. . |
| 0325289 | 7/1989 | European Pat. Off. . |
| 0340013 | 11/1989 | European Pat. Off. . |
| 0367339 | 5/1990 | European Pat. Off. . |
| 0384070 | 8/1990 | European Pat. Off. . |
| 0390251 | 10/1990 | European Pat. Off. . |
| 0420317 | 4/1991 | European Pat. Off. . |
| 0458397 | 11/1991 | European Pat. Off. . |
| 0458398 | 11/1991 | European Pat. Off. . |
| 0509787 | 10/1992 | European Pat. Off. . |
| 0523956 | 1/1993 | European Pat. Off. . |
| 0523956 B1 | 1/1993 | European Pat. Off. . |
| 0 540 784 | 5/1993 | European Pat. Off. . |
| 1429143 | 3/1976 | United Kingdom . |
| 1437950 | 6/1976 | United Kingdom . |
| 1470250 | 4/1977 | United Kingdom . |
| 1473201 | 5/1977 | United Kingdom . |
| 1473202 | 5/1977 | United Kingdom . |
| 2123044 | 1/1984 | United Kingdom . |
| 89/09813 | 10/1989 | WIPO . |
| 94/25591 | 11/1994 | WIPO . |
| 95/07972 | 3/1995 | WIPO . |
| 95/29996 | 11/1995 | WIPO . |
| 96/03369 | 2/1996 | WIPO . |
| 9603369A1 | 2/1996 | WIPO . |
| 97/04102 | 2/1997 | WIPO . |

OTHER PUBLICATIONS

Chemical abstract No. 111:99318, abstract of an article by Shiozaki et al entitled "Photostabilizing efficiency and application of nickel compounds to dyed leathers", Chem. Express 4(5), 365–8, 1989, No Month.

PCT; International Search Report; Dated Nov. 12, 1998; EP 98/03438.

Wilkinson et al., Rate Constants for the Decay and Reactions of the Lowest Electronically Excited Singlet State of Molecular Oxygen in Solutions. An Expanded and Revised Compilation. (J. Phys.Chem. Ref. Data, vol. 24, No. 2, pp. 663–1021, 1995), No Month.

Gorman, "The Biomolecular Reactivity of Singlet Molecular Oxygen", (Advances In Photo Chemistry, vol. m , pp. 217–274, 1992), No Month.

Ogawa et al., "Determination Method Of Singlet Oxygen In The Atmosphere By Use Of α–Terpinene", (Chemosphere, vol. 22, No. 12, pp. 1211–1225, 1991), No Month.

*Primary Examiner*—Anthony Green
*Attorney, Agent, or Firm*—Neil Y. Gilbert, Esq.

[57] ABSTRACT

A photofading inhibitor compound comprising a singlet oxygen quenching moiety having a quenching rate of $1\times10^6$ L mol$^{-1}$S$^{-1}$ or faster and a cationic moiety.

12 Claims, No Drawings

PHOTOFADING INHIBITOR DERIVATIVES AND THEIR USE IN FABRIC TREATMENT COMPOSITIONS

TECHNICAL FIELD

The present invention relates to fabric washing detergent compositions. In particular, the invention relates to fabric washing detergent compositions containing photofading inhibitors.

BACKGROUND AND PRIOR ART

The fading of coloured fabrics by sunlight during wear and during drying is a major problem for consumers in many parts of the world, thus susceptible fabrics especially fabrics from temperate and low latitude regions and the tropics, can be severely faded. Sun fading of fabrics is of specific concern to consumers because the contrast between exposed and unexposed areas makes it particularly noticeable. e.g on collars, inside versus outside of garments, and on wrap around garments such as saris. The textile industry has made extensive efforts to develop light stable dyes and after-treatments to protect the dyes; however the fading of fabric still remains a problem.

The use of certain sunscreens has already been discussed in the literature. U.S. Pat. No. 4,788,054 (Bernhardt) teaches the use of N-phenylphthalisomides as ultraviolet radiation absorbers for cotton, wool, polyester and rayon. The compositions require an aqueous sulphuric acid vehicle for deposition. Fabric care compositions comprising a water dispersible/water soluble copolymers which prevent photofading are disclosed in EP 0 523 956 (Unilever). WO 96/03369 (Procter and Gamble) discloses the use of butylated hydroxy toluene for the protection of surfaces from physical and chemical degradation.

However the major problem that needs to be overcome is how to deposit photofading inhibitors onto fabric during the wash using a detergent containing washing system, which is designed to suspend particulate materials and solubilise oils.

The present invention relates to new photofading inhibitors that deposit easily onto fabric during the wash process.

DEFINITION OF THE INVENTION

Accordingly the present invention discloses a photofading inhibitor compound comprising a singlet oxygen quenching moiety having a quenching rate of $1 \times 10^6$ L mol$^{-1}$S$^{-1}$ or faster and a cationic or zwitterionic moiety.

The invention further discloses a fabric treatment composition comprising:

i) a cationic surfactant, and/or an anionic surfactant, and/or a nonionic surfactant, and/or zwitterionic surfactant and/or a fabric softening compound and a ii) an photofading inhibitor compound as discussed above The invention also relates to a method of preparing a photofading inhibitor compound comprising the steps of:

i) selecting a singlet oxygen quencher ii) selecting a partially water soluble linking group iii) reacting the singlet oxygen quencher with the partially water soluble linking group iv) selecting a cationic or zwitterionic moiety v) reacting the cationic zwitterionic moiety (iv) with the product of step (iii).

DETAILED DESCRIPTION OF THE INVENTION

Photofading Inhibitor

Without being bound by theory it is thought that the extent of individual dye fading is dependent on the light wavelength. Some dyes are photodegraded primarily by the UV component of solar radiation, for other dyes the visible component of solar radiation is the main cause of colour loss, whilst others are equally affected by both visible and UV radiation.

Protection against solar radiation can be achieved with UVA and UVB absorbing materials with high extinction coefficients. These compounds are commonly called sunscreens. However, the use of such materials is preferably limited for protection against UV radiation with a wavelength of 400 nm or below as compounds with the whole or part of their spectra above 400 nm will be coloured.

Protection from visible radiation with a wavelength of 400 nm or greater is preferably achieved by using singlet oxygen quenchers, free radical traps and anti-oxidants.

Without being bound by theory the photofading inhibitor compounds of the present invention are thought to be effective in preventing photofading of fabric due to the fact that they are at least partially water soluble and are substantive to cotton surfaces.

The photofading inhibitor of the invention comprises a singlet oxygen quencher having a quenching rate of at least $1 \times 10^6$ L mol$^{-1}$S$^{-1}$, preferably $1 \times 10^8$ L mol$^{-1}$S$^{-1}$ or faster, most preferably $1 \times 10^{10}$ L mol$^{-1}$S$^{-1}$ or faster.

The quenching rate of singlet oxygen can be measured using a variety of techniques; (see reference S. Ogawa et. al. Chemosphere 1991, 22(12), 1211–25.) or physically (See A. A. Gorman, Advances in Photochemistry, Volume 17, 217–274).

The method reported in F. Wilkinson et. al. in Journal of Physical and Chemical Reference Data 1993, vol 24, No 2, pp 663–1021. incorporated herein by reference was used to determine the quenching rate to prevent fading. This quenching rate was measured by fluorescence lifetime measurements using the 1270 nm fluorescence peak.

The photofading inhibitor of the invention comprises a moiety having a positive charge, ie. a cationic or zwitterionic moiety.

The term zwitterionic as used herein regers to molecules that contain both an anionic and cationic functionality at the same time.

The photofading inhibitor of the invention comprises a cationic or zwitterionic moiety. It is preferred if the cationic or zwitterionic moiety is a quaternary ammonium group. For cationic moieties the quaternary ammonium group may be part of a cyclic ring for example 1,4 diazabicyclo[2.2.2]octane or have the structure $N^+(R^1)_3$ in which each $R^1$ group is independently selected from a $C_{1-6}$ alkyl or $C_{2-6}$ alkenyl group. For zwitterionic moieties the quaternary ammonium group may be part of a cyclic ring or have the structure $N^+(R^1)_2$ in which each $R^1$ group is independently selected from a $C_{1-6}$ alkyl or $C_{2-6}$ alkenyl group.

It is preferred if the cationic moiety is a quaternary ammonium group which is an N,N,N-trialkyl group, especially N,N,N-trimethyl group or the zwitterionic moiety is a quaternary ammonium group which is an N,N dialkyl group, especially N,N-dimethyl. Preferred zwitterionic are those having an N,N,-dimethylpropyl group.

Due to there good properties in reducing photofading of fabrics it is preferred if the singlet oxygen quencher moiety is a substituted phenol, cycloalkene or an unsaturated heterocycle.

Suitable oxygen quenching moieties are selected from the group consisting of phorophyrins, phthalocyanins, vitamin E derivatives, furans, terpinenes, cyclopentadiens, benzofurans, catechols, cyclohanones, anthracenes and cyclohexadienes. Benzefuran has been found to be especially suitable.

It is especially preferred if the furan is benzofuran.

It is further preferred if the singlet oxygen quencher moiety of the photofading inhibitor comprises a cyclic group. The cyclic group preferably consists of a carbon ring, the carbon ring may be interrupted with one or more N, or O atoms. It is advantageous if the cyclic group (including the N or O atoms) comprises a 5 or 6 membered ring.

It is preferred that if present the cyclic group is substituted, the degree of substitution is preferably at least 2, more preferably at least 3, most preferably 4 or more.

The groups with which the cyclic group is substituted are preferably a $C_{1-8}$ alkyl group or a $C_{2-8}$ alkenyl group, or derivatives thereof. Examples of suitable substituents include methyl, ethyl, propyl, butyl, pentyl and hexyl groups. The groups may be cyclic and/or aromatic.

The oxygen quenching moiety is preferably a diene or especially preferred a triene.

Examples of suitable oxygen quenching moieties are given in F. Wilkinson et. al. in Journal of Physical and Chemical Reference Data 1993, vol 24, No 2, pp 663–1021.

It is preferable if the singlet oxygen quencher is present at levels from 0.005 wt % to 5 wt %, of the total composition more preferably 0.01 wt % to 1.0 wt % of the total composition most preferably 0.02 wt % to 0.5wt %.

It is preferable if the singlet oxygen quenching moiety is linked to the cationic moiety via an ester or amide linkage. During the synthesis of these molecules these linkages are formed by reacting the singlet oxygen quenching moiety with an alkyl amine or an alkyl alcohol.

A method of preparing a photofading inhibitor is also provided comprising the steps (i) to (v) a recited above. It is preferred if the partially water soluble linking group is either an alkyl amine or an alkyl alcohol which is capable of forming an amide or an ester link within the photofading inhibitor compound. The present invention also relates to compositions comprising the photofading inhibitor described above.

The Surfactant/Fabric Softening Compound

Compositions according to the invention contain a cationic surfactant, and/or an anionic surfactant, a nonionic surfactant, a zwitterionic surfactant and/or a fabric softening compound, in addition to the photofading inhibitor.

It is preferred if compositions of the invention include a nonionic surfactant or system. Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

It is preferred if the level of nonionic surfactant is from 2 wt % to 40 wt %, preferably from 10 wt % to 30 wt % of the total product.

The choice of detergent-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The present invention is particularly advantageous in that it allows anionic surfactant to be present in the formulation, however in some instances it is preferable if anionic surfactant is absent.

Suitable anionic surfactants are well-known to those skilled in the art and include alkylbenzene sulphonate primary and secondary alkyl sulphates, particularly $C_8$–$C_{15}$ primary alkyl sulphates; alkyl ether sulphates; olefin sulphonates; alkyl xylene sulphonates; dialkyl sulphosuccinates; ether carboxylates; isothionates; sarcosinates and fatty acid ester sulphonates. Sodium salts of the anionic surfactants are generally preferred.

Detergent compositions suitable for use in most automatic fabric washing machines generally contain anionic non-soap surfactant, or nonionic surfactant, or combinations of the two in any ratio, optionally together with soap.

For compositions in solid form, especially powder, the detergent surfactant is advantageously solid at room temperature as this provides crisp composition particles.

The compositions of the invention may contain a cationic compound. Most preferred are quaternary ammonium compounds.

It is advantageous if the quaternary ammonium compound is a quaternary ammonium compound having at least one $C_{12}$–$C_{22}$ alkyl chain.

Preferred cationic compounds include the quaternary ammonium compound having the following formula:

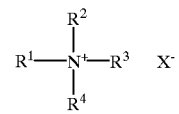

in which $R^1$ and $R^2$ are independently selected from $C_{12}$ to $C_{22}$ alkyl or alkenyl chain; $R^3$ and $R^4$ are independently selected from $C_1$–$C_4$ alkyl chains and $X^-$ is a compatible anion.

Other suitable quaternary ammonium compounds are disclosed in EP 0 239 910 (Procter and Gamble).

The cationic compound may be present from 0.02 wt % to 20 wt % of the total weight of the composition.

Preferably the cationic compound may be present from 3 wt % to 99 wt %, a more preferred composition range is from 3 wt % to 30 wt %, and most preferably the composition range is from 3 wt % to 25 wt % of the total weight of the composition.

Detergency Builder

The detergent compositions of the invention will generally also contain one or more detergency builders or electrolytes. The total amount of detergency builder in the compositions will suitably range from 5 to 80 wt %, preferably from 10 to 60 wt %.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst).

Inorganic phosphate builders, for example, sodium orthophosphate, pyrophosphate and tripolyphosphate are especially suitable for use with this invention.

The detergent compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50 wt %.

The alkali metal aluminosilicate may be either crystalline or amorphous or mixtures thereof, having the general formula:

$$0.8\text{--}1.5\ Na_2O.\ Al_2O_3.\ 0.8\text{--}6\ SiO_2$$

These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature.

Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20.

Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Bleach Components

Detergent compositions according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 0.1 to 35 wt %, preferably from 0.5 to 25 wt %.

The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernonanoic acid precursors. Especially preferred bleach precursors suitable for use in the present invention are N,N,N',N'-tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. Examples of such peracids can be found in U.S. Pat. No. 4,686,063 and U.S. Pat. No. 5,397, 501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1–12%, preferably 0.5–10%.

A bleach stabiliser (heavy metal sequestrant) may also be present. Suitable bleach stabilisers include ethylenediamine tetraacetate (EDTA), the polyphosphonates such as Dequest (Trade Mark) and non-phosphate stabilisers such as EDDS (ethylene diamine di-succinic acid). These Bleach stabilisers are also useful for stain removal, especially in products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

The Enzyme

The compositions of the invention may contain an Enzyme. Preferred enzymes include the proteases, amylases, cellulases, oxidases, and peroxidases usable for incorporation in detergent compositions.

Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Detergency enzymes are commonly employed in granular form in amounts of from about 0.1 to about 3.0 wt %.

Other Ingredients

The compositions of the invention may contain alkali metal, preferably sodium carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate polymer, or sodium silicate.

One preferred powder structurant is fatty acid soap, suitably present in an amount of from 1 to 5 wt %.

Other materials that may be present in detergent compositions of the invention include sodium silicate; antiredeposition agents such as cellulosic polymers; inorganic salts such as sodium sulphate; lather control agents or lather boosters as appropriate; proteolytic and lipolytic enzymes; dyes; coloured speckles; perfumes; foam controllers; fabric softening compounds, soil release polymers, fluorescers and decoupling polymers. This list is not intended to be exhaustive.

If a detergent composition, the detergent composition when diluted in the wash liquor (during a typical wash cycle) will give a pH of the wash liquor from 7 to 10.5.

The components of the present invention may be incorporated in detergent compositions of all physical types, for example, powders, liquids, gels and solid bars.

Compositions of the invention may be prepared by any suitable method.

Particulate compositions are suitably prepared by spray-drying a slurry of compatible heat-insensitive ingredients, and then spraying on or postdosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l.

Especially preferred compositions have bulk densities of at least 650 g/liter, more preferably at least 700 g/liter.

Such powders may be prepared either by post-tower densification of spray-dried powder, or by wholly non-tower methods such as dry mixing and granulation; in both cases a high-speed mixer/granulator may advantageously be used.

Processes using high-speed mixer/granulators are disclosed, for example, in EP 340 013A, EP 367 339A, EP 390 251A and EP 420 317A (Unilever).

Liquid compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent or softening active.

The fabric treatment composition may also be in the form of a bar or a paste.

The invention will now be illustrated with reference to the following non-limiting Examples. Further modifications within the scope of the present invention will be obvious to the man skilled in the art.

Comparative examples are illustrated by a letter and examples of the invention are illustrated by a number.

SYNTHESIS OF COMPOUNDS

Compound 1; 3,4-dihydro-6-acetyl-2,5,7,8-tetramethyl-1-benzopyran-2-(N,N,N-trimethyl-2-aminoethyl)carbamide To prepare the Singlet Oxygen Quencher Precursor;

To a 1 liter round bottom flask with an atmosphere of di-nitrogen was added dry pyridine (10.00 g, excess mole) and dry THF solvent to dissolve 3,4-dihydro-6-hydroxy-2,5,7,8-tetramethyl-1-benzopyran-2-carboxylate (24.9 g). The temperature was reduced to 0° C. and acetyl chloride (15 ml) slowly added with agitation. The solution was observed to be yellow. The solution was allowed to warm up to ambient temperature and then refluxed for 1 hour. The solution was cooled, reduced in volume (100 ml) and water added with a sodium hydrogen carbonate (1 g). The solution was extracted three times with DCM, the DCM dried (sodium sulphate) and evaporated to dryness. The hydroxy acetyl was redissolved in dry THF (100 ml) and oxalyl chloride (10% solution 50 ml, excess) was slowly added at 10° C. under an atmosphere of di-nitrogen. The solution was allowed to warm to ambient temperature and stirred for 12 hours. The clear solution was evaporated to dryness at 50° C. and 10 mbar to give 3,4-dihydro-6-acetyl-2,5,7,8-tetramethyl-1-benzopyran-2-carbonyl chloride. The solid was washed with saturated sodium bicarbonate and vacuum dried. A carbon 13 NMR clearly showed the aromatic ring and the acetyl functionality.

Singlet Oxygen Quencher and Linking Group

To a 1 liter round bottom flask with an atmosphere of di-nitrogen was added and dry THF solvent to dissolve 3,4-dihydro-6-acetyl-2,5,7,8-tetramethyl-1-benzopyran-2-carbonyl chloride. N,N-dimethyldiaminoethane was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three times with dichloromethane (DCM). The DCM was dried (sodium sulphate) and evaporated to dryness.

Singlet Oxygen Quencher/Linking Group/Cationic

The resultant amide prepared above was quaternised with methyl tosylate in tetrahydofuran (THF) at reflux for 1 hour. The solution was cooled, evaporated to dryness and recrystallised from water:ethanol (1:1). The solid was submitted to NMR analysis C13 and H1 which confirmed the synthesis of compound 1.

Compound 2; 3,4-dihydro-6-acetyl-2,5,7,8-tetramethyl-1- benzopyran-2-(N,N,N-trimethyl-2-aminopropyl)carbamide To prepare the Singlet Oxygen Quencher Precursor the method of compound 1 was followed.

Singlet Oxygen Quencher and Linking Group

To a 1 liter round bottom flask with an atmosphere of dinitrogen was added and dry THF solvent to dissolve 3,4-dihydro-6-hydroxy-2,5,7,8-tetramethyl-1-benzopyran-2-carbonyl chloride. N,N-dimethyldiaminopropyl was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three times with DCM. The DCM was dried (sodium sulphate) and evaporated to dryness.

Singlet Oxygen Quencher/Linking Group/Cationic

The resultant amide prepared above was quaternised with methyl iodide in THF at reflux for 1 hour. The solution was cooled, evaporated to dryness and recrystallised from water:ethanol (1:1). The solid was submitted to NMR analysis C13 and H1 which confirmed the synthesis of compound 2.

Compound 3; 3,4-dihydro-6-acetyl-2,5,7,8-tetramethyl-1-benzopyran -2-ethyl-DABCO To prepare the Singlet Oxygen Quencher Precursor the method of compound 1 was followed.

Singlet Oxygen Quencher and Linking Group with Quencher

To a 1 liter round bottom flask with an atmosphere of dinitrogen was added and dry THF solvent to dissolve 3,4-dihydro-6-hydroxy-2,5,7,8-tetramethyl-1-benzopyran-2-carbonyl chloride. 1,4-diazocycloocta[2.2.2.]ane-N, ethylamine was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three times with DCM. The DCM dried (sodium sulphate) and evaporated to dryness.

Compound 4; 3,4-dihydro-6-acetyl-2,5,7,8-tetramethyl-1-benzopyran-2-(N,N,-dimethyl-N-propyl-2-aminopropyl)carbamide To prepare the Singlet Oxygen Quencher Precursor the method of compound 1 was followed.
Singlet Oxygen Quencher and Linking Group To a 1 liter round bottom flask with an atmosphere of dinitrogen was added and dry THF solvent to dissolve 3,4-dihydro-6-hydroxy-2,5,7,8-tetramethyl-1-benzopyran-2-carbonyl chloride. N,N-dimethyldiaminopropyl was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three times with DCM, the DCM dried (sodium sulphate) and evaporated to dryness.
Singlet Oxygen Quencher/Linking Group/Cationic The resultant amide prepared above was quaternised with propyl iodide in THF at reflux for 1 hour. The solution was cooled, evaporated to dryness and recrystallised from water:ethanol (1:1). The solid was submitted to NMR analysis C13 and H1 which confirmed the synthesis of compound 4.

Compound 5; 3,4-dihydro-6-acetyl-2.5,7.8-tetramethyl-1-benzopyran-2-(N,N,N-trimethyl-2-aminopropyl)carboxylate ester To Prepare the Singlet Oxygen Quencher Precursor the method of compound 1 was followed.
Singlet Oxygen Quencher and Linking Group To a 1 liter round bottom f;ask with an atmosphere of dinitrogen was added and dry THF solvent to dissolve 3,4-dihydro-6-hydroxy-2,5,7,8-tetramethyl-1-benzopyran-2-carbonyl chloride. N,N-dimethylaminoethylalcohol was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three times with DCM. The DCM dried (sodium sulphate) and evaporated to dryness.
Singlet Oxygen Quencher/Linking Group/Cationic The resultant ester prepared above was quaternised with methyl iodide in THF at reflux for 1 hour. The solution was cooled, evaporated to dryness and recrystallised from water:ethanol (1:1). The solid was submitted to NMR analysis C13 and H1 which confirmed the synthesis of Compound 5. This compound was also made directly from choline.

Compound 6; 3,4-dihydro-6-acetyl-2,5,7,8-tetramethyl-1-benzopyran-2-(N'-acetyl-2,6-disulphonic diamino stilbene)carbamide To prepare the Singlet Oxygen Quencher Precursor the method of compound 1 was followed.
Singlet Oxygen Quencher and Linking Group To a 1 liter round bottom flask with an atmosphere of dinitrogen was added and dry THF solvent to dissolve 3,4-dihydro-6-hydroxy-2,5,7,8-tetramethyl-1-benzopyran-2-carbonyl chloride. N-acetyl-2,6-disulphonicdiamonostillbene was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three time with DCM, the DCM dried (sodium sulphate) and evaporated to dryness.

Compound 7; 3,4-dihydro-6-hydroxy-2,5,7,8-tetramethyl-1-benzopyran-2-carboxyamidepropyl-(N,N,-dimethylpropylsulphate)

A zwitterionic derivative

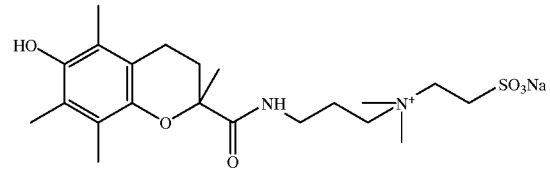

To a 1 liter round bottom flask with an atmosphere of dinitrogen was added dry THF solvent to dissolve 3,4-dihydro-6-hydroxy-2,5,7,8-tetramethyl-1-benzopyran-2-carbonyl chloride (2.68 g, 10 mmole), N,N-dimethyldiaminopropane (1.1 g, 11 mmole) was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three time with DCM, the DCM dried (sodium sulphate) and evaporated to dryness. The resultant amide was quaternised with propane sulfone in THF at reflux for 1 hour. The solution was cooled, evaporated to dryness and recrystalised from water:ethanol (1:1). The solid was submitted for NMR analysis (C13 and H1).

Compound 8; Benzofuran-2-carboxyamide(N,N,N-trimethylpropylammonium) mesolate.

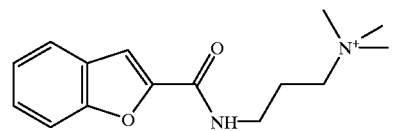

To a 1 liter round bottom flask with an atmosphere of dinitrogen was added dry THF solvent to dissolve benzofuran-2-carbonyl chloride (1.80 g, 10 mmole), N,N-dimethyldiaminopropane (1.1 g, 11 mmole) was dissolved in dry THF and slowly added to the solution in the flask at 0° C. with agitation. The solution was allowed to reach ambient temperature and then stirred for 12 hours. The solution was reduced in volume, water with sodium bicarbonate added and the solution extracted three time with DCM, the DCM dried (sodium sulphate) and evaporated to dryness. The resultant amide was quaternised with dimethylsulphate in THF at reflux for 1 hour. The solution was cooled, evaporated to dryness and recrystalised from water:ethanol (1:1). The solid was submitted for NMR analysis (C13 and H1).
Testing Methodology—Compounds 1 to 6

The Compound of interest was dissolved in water and the dyed cloth was added to this solution (Dyed with Cibacron Red FB at 0.1% weight of the fabric dye). The weight of Compound added to the water was 0.1% of the weight of dry, dyed cloth added. The solution was agitated for 15 minutes. The cloth was removed from the solution and wrung. The cloth was air dried at ambient temperature and then placed in a Atlas weather-o-meter and subjected to 20 hours irradiation following the guidelines outlined in "Methods of Test for Colour Fastness for Textiles and Leather" Under B02: Colour fastness to artificial Light under BS 1006:1990.

The reflectance of the cloth was read using a Spectra flash 500 before and after exposure to sunlight. The fade/% is referenced to Example A i.e.
Reflectance of Example A—Reflectance of Example to be tested ×100
Reflectance of Example A

EXAMPLES A TO E AND EXAMPLES 1 TO 3

The following Examples were evaluated
Example A—Untreated fabric not immersed in water.
Example B—Parsol MCX.
Example C—Fabric added to water with no photophading inhibitor present.
Example D—Fabric added to a solution of terpinene.
Example E—Fabric added to a solution of furan.
Example 1—Fabric added to a solution of Compound 1.
Example 2—Fabric added to a solution of Compound 2.
Example 3—Fabric added to a solution of Compound 3.

TABLE 1

| | Example | | | | | | |
|---|---|---|---|---|---|---|---|
| A. | B | C | D | E | 1 | 2 | 3 |
| Rate cons — | $1 \times 10^4$ | $2 \times 10^5$ | $1 \times 10^8$ | $2 \times 10^8$ | $5 \times 10^8$ | — | $1 \times 10^9$ |
| Fade/% 100 | 100 | 100 | 70 | 80 | 30 | 25 | 20 |

Table 1 thus demonstrates that Examples of the invention prevent fading of coloured articles.

EXAMPLES 4, 5 AND EXAMPLES G,F

A wash solution (1 liter) was made up consisting of 0.5 g (LAS) and 0.5 g (nonionic)(Synperonic A7 ex Shell). To the solution was added sodium carbonate (1 g).

To give Example 4 Compound 1 (0.05 g in 10 ml water) was added to 100 ml of surfactant stock solution.

To give Example G vitamin E acetate (0.05 g in 10 ml water) was added to 100 ml of surfactant stock solution.

Example F comprised the stock solution without the any further additive.

Example 5 was similar to Example 4, however the anionic surfactant was substituted for nonionic surfactant in the stock solution giving a total of 1 g/L of nonionic surfactant.

Test cloths (dyed with Cibacron Red FB at 0.1% wof dye.) were washed in these Examples at 40° C. for 30 minutes at 60 revs per minute in a tergometer pot. The cloths were rinsed 5 times. The cloths were placed in a weatherometer for 20 hours each and the reflectance spectra measured.

TABLE 2

| | Example F | Example G | Example 5 | Example 4 |
|---|---|---|---|---|
| Fade DR | 4.2 | 4.2 | 2.1 | 3.9 |
| % fade | 100 | 100 | 55 | 93 |

EXAMPLES 6,7 and 8

Testing Methodology

Compound 7 (Example 6) was tested against compound 1 (Example 7) and compound 8 (Example 8) to investigate the suitability of zwitterionic moieties in the photofading inhibitor compounds.

The method used is as given below:
The comparison of cationic and zwitterionic derivatives was evaluated using the same red test cloth as before.

1. Standard wash solutions of LAS (1 g/l) and STP (3 g/l) were made up. 250 ml was placed in tergometry beakers. A control of 250 ml of water (demin) was also placed in tergometry pots.
2. to the solutions in 1 above was added 0.01 g or 0.1 g of cationic singlet oxygen quencher or the zwitterionic. The solutions were heater to 40 C. and 20 g of cibacron red FB cloth added and washed for 30 mins at 100 revs a minute.
3. The dry cloths were placed in a Atlas weatherometer for 20 hours and the degree of fading assessed by the change in reflectance as measured by a Spectraflash 500.

The test cloth used was the same as in Examples 1 to 5 and the methodology used to determine the Fade % was that described above. The control samples were as before.

TABLE 3

| | Example 6 | Example 7 | Example 8 |
|---|---|---|---|
| Percentage fade (+/− 2%) | Compound 7 1.0 mM | Compound 1 1.0 mM | Compound 8 1.0 mM |
| Water | 80 | 82 | 75 |
| LAS/STP | 77 | 89 | 76 |

The above demonstrates the suitability of zwitterionic moieties in the photofading inhibitor compounds of the present invention.

I claim:

1. A photofading inhibitor compound comprising a molecule having:
   (i) a singlet oxygen quenching group having a quenching rate of $1 \times^6$ L mol$^{-1}$S$^{-1}$ or faster, said singlet oxygen quenching group being a substituted phenyl, cycloalkene or an unsaturated heterocycle; and
   (ii) a cationic or zwitterionic moiety comprising a quaternary ammonium group.

2. A photofading inhibitor according to claim 1 in which the singlet oxygen quencher has a quenching rate of $1 \times 10^8$ L mol$^{-1}$ S$^{-1}$ or faster.

3. A photofading inhibitor according to claim 1 in which the quaternary ammonium group is an N,N,N-trimethyl group or N,N di methyl group.

4. A photofading inhibitor according to claim 1 in which the singlet oxygen quenching group comprises a 5 or 6 membered ring.

5. A photofading inhibitor according to claim 4 in which the singlet oxygen quenching group comprises a substituted cyclic group having a degree of substitution of at least 3.

6. A photofading inhibitor according to claim 5 in which the cyclic group is substituted with a $C_{1-8}$ alkyl group or a $C_{2-8}$ alkenyl group, or derivatives thereof.

7. A photofading inhibitor according to claim 1 in which the singlet oxygen quenching group is selected from the group consisting of phorphyrins, phthalocyanins, soluble vitamin E derivatives, furans, terpinenes, and cyclohexadienes.

8. A photofading inhibitor according to claim 7 in the singlet oxygen quenching group is selected from the group consisting of benzofurans.

9. A fabric treatment composition comprising:

i) a component selected from the group consisting of 0.02–20% by weight of a cationic detergent-active compound, an anionic detergent-active compound, 2–40% by weight of a nonionic detergent-active compound, a zwitterionic detergent-active compound and mixtures thereof; and ii) a photofading inhibitor compound according to claim 1 wherein the photofading inhibitor compound is present at a level such that said singlet oxygen quenching group is present at a level of 0.005 to 5% by weight based on the total composition.

10. A fabric treatment composition according to claim 9 in which the composition further comprises from about 5 to about 80 wt. % based on the total composition of electrolyte or detergency builder.

11. A method of preparing a photofading inhibitor compound comprising the steps of:

i) selecting a singlet oxygen quencher selected from the group consisting of substituted phenols, cycloalkenes and unsaturated heterocycles;

ii) selecting a partially water soluble linking group;

iii) reacting the singlet oxygen quencher with the partially water soluble linking group;

iv) selecting a cationic or zwitterionic moiety comprising a quaternary ammonium group; and v) reacting the cationic or zwitterionic moiety selected in step (iv) with the product of step (iii).

12. A method of preparing a photofading inhibitor compound according to claim 11 in which the partially water soluble linking group is either an alkyl amine or an alkyl alcohol, said alkyl amine or alkyl alcohol forming in step v) an amide or an ester link within the product of step iii).

* * * * *